United States Patent
Carr et al.

[11] Patent Number: 5,462,537
[45] Date of Patent: Oct. 31, 1995

[54] ABSORBENT ARTICLE WITH INVERSELY RELATED GRADIENTS

[75] Inventors: James M. Carr, Kaukauna; Elwood W. Harke, Kimberly, both of Wis.

[73] Assignee: Kimberly-Clark Corporation, Neenah, Wis.

[21] Appl. No.: 738,698

[22] Filed: Jul. 31, 1991

[51] Int. Cl.$^6$ .................................................. A01F 13/15
[52] U.S. Cl. ........................... 604/368; 604/370; 604/378
[58] Field of Search ................................. 604/368, 370, 604/378–384, 385.1, 365, 366, 374, 369

[56] References Cited

U.S. PATENT DOCUMENTS

| | | | |
|---|---|---|---|
| Re. 29,789 | 10/1978 | Kolback | 128/284 |
| 1,702,530 | 2/1929 | Williams . | |
| 3,073,309 | 1/1963 | Mosier | 128/290 |
| 3,121,427 | 2/1964 | Mosier | 128/284 |
| 3,669,103 | 6/1972 | Harper et al. | 128/156 |
| 3,670,731 | 6/1972 | Harmon | 128/284 |
| 3,769,978 | 11/1973 | DeNight et al. | 604/380 |
| 3,848,598 | 11/1974 | Mesek | 128/287 |
| 3,881,488 | 5/1975 | DeLanty et al. | 128/287 |
| 3,888,257 | 6/1975 | Cook et al. | 128/296 |
| 3,968,798 | 7/1976 | Hokanson | 128/284 |
| 4,087,506 | 5/1978 | Cook et al. | 264/112 |
| 4,103,062 | 7/1978 | Aberson et al. | 428/283 |
| 4,105,033 | 8/1978 | Chatterjee et al. | 128/285 |
| 4,144,886 | 3/1979 | Holst et al. | 1238/284 |
| 4,186,165 | 1/1980 | Aberson et al. | 264/112 |
| 4,213,459 | 7/1980 | Sigl et al. | 604/380 |
| 4,226,237 | 10/1980 | Levesque | 128/285 |
| 4,333,462 | 6/1982 | Holtman et al. | 128/287 |
| 4,333,463 | 6/1982 | Holtman | 128/287 |
| 4,333,465 | 6/1982 | Wiegner | 128/290 R |
| 4,381,782 | 5/1983 | Mazurak et al. | 604/368 |
| 4,381,783 | 5/1983 | Elias | 604/368 |
| 4,410,324 | 10/1983 | Sabee | 604/368 |
| 4,449,979 | 5/1984 | Holtman | 604/379 |
| 4,468,428 | 8/1984 | Early et al. | 428/221 |
| 4,500,315 | 2/1985 | Pieniak et al. | 604/379 |
| 4,501,586 | 2/1985 | Holtman | 604/380 |
| 4,537,590 | 8/1985 | Pieniak et al. | 604/379 |
| 4,557,777 | 12/1985 | Sabee | 156/201 |
| 4,559,050 | 12/1985 | Iskra | 604/368 |
| 4,573,988 | 3/1986 | Pieniak et al. | 604/379 |
| 4,578,068 | 3/1986 | Kramer et al. | 604/368 |
| 4,585,448 | 4/1986 | Enloe | 604/378 |
| 4,673,402 | 6/1987 | Weisman et al. | 604/368 |
| 4,685,909 | 8/1987 | Berg et al. | 604/360 |
| 4,685,915 | 8/1987 | Hasse et al. | 604/378 |
| 4,699,823 | 10/1987 | Kellenberger et al. | 428/219 |
| 4,718,901 | 1/1988 | Singheimer | 604/385 A |
| 4,798,602 | 1/1989 | Laus | 604/372 |
| 4,828,555 | 5/1989 | Hermansson | 604/379 |
| 4,834,735 | 5/1989 | Alemany et al. | 604/368 |
| 4,997,428 | 3/1991 | Linnebur et al. | 604/368 |
| 5,017,324 | 5/1991 | Kaiser et al. | 264/510 |
| 5,087,506 | 2/1992 | Palumbo | 604/368 |

FOREIGN PATENT DOCUMENTS

| | | |
|---|---|---|
| 0320991A2 | 12/1988 | European Pat. Off. . |
| 0325416 | 7/1989 | European Pat. Off. ............. 604/368 |
| 0397110A2 | 5/1990 | European Pat. Off. . |
| 2437826 | 10/1979 | France . |
| 1406615 | 9/1975 | United Kingdom . |
| 2144995 | 3/1985 | United Kingdom . |
| 2145661 | 4/1985 | United Kingdom . |
| 2175024 | 7/1988 | United Kingdom . |

*Primary Examiner*—Randall L. Green
*Assistant Examiner*—K. M. Reiche
*Attorney, Agent, or Firm*—Douglas L. Miller; Kimberly-Clark Corporation

[57] ABSTRACT

An absorbent article is provided with inversely related basis weight and density gradients for absorbing and retaining body liquids. A central target area of the absorbent article has an average higher basis weight and a lower average density than end areas. Superabsorbent material is selectively disposed within the article.

3 Claims, 5 Drawing Sheets

ABSORBENT ARTICLE WITH INVERSELY RELATED GRADIENTS

BACKGROUND OF THE INVENTION

This invention pertains to disposable absorbent articles, and more particularly to disposable absorbent articles having inversely related basis weight and density gradients.

Various disposable articles utilize absorbent structures to absorb and retain liquids, such as urine. Extensive research efforts have been directed to increasing the amount of liquids absorbed for a given amount of absorbent material, so that the absorbent article may be made in a smaller or thinner shape.

One method of reducing or thinning the shape is to vary the amounts of absorbent material within the absorbent article. One past attempt has included an absorbent article comprising an intermediate region that has a higher basis weight and higher density than its end regions. Another attempt has included an absorbent article comprising an intermediate region that has a lower basis weight and lower density than its end regions. Still another attempt has included an absorbent article comprising an intermediate region having a higher basis weight than its end areas.

Another method of reducing or thinning the shape of an absorbent article is to reduce the amount of fibrous material, such as cellulosic fibers, and to add superabsorbent material.

Notwithstanding the above methods, there still exists a need for an improved absorbent article.

SUMMARY OF THE INVENTION

In one form of the present invention there is provided an absorbent article comprising a layer having generally oppositely disposed end areas, a target area between the end areas, and top and bottom surfaces defining a layer thickness. The layer includes an absorbent fibrous material and particles of superabsorbent material in which at least a portion of the particles are in a discrete lamina. The target area has a higher average basis weight and a lower average density than one of the end areas.

In another form of the present invention there is provided a pant article comprising a main body including a front, a back, a crotch, and a pair of sides forming a waist opening, a pair of leg openings, and an interior space. An absorbent structure is in the interior space and comprises opposite end areas and a target area between the end areas. The target area has a higher average basis weight and a lower average density than the end areas.

BRIEF DESCRIPTION OF THE DRAWINGS

The above-mentioned and other features and objects of this invention and the manner of attaining them will become more apparent, and the invention itself will be better understood by reference to the following description of the invention, taken in conjunction with the accompanying drawings, wherein.

DESCRIPTION OF A PREFERRED EMBODIMENT

Within the context of this specification, each term below will include the following meaning:

(a) "Disposed", "disposed on", "disposed with", "disposed at", and variations thereof are intended to mean that one element can be integral with another element, or that one element can be a separate structure joined to or placed with or placed near another element.

(b) "Particles" as used with superabsorbent particles (SAP) or superabsorbent material (SAM) means any geometric form such as, but not limited to, spherical grains, cylindrical fibers or strands, flat surfaces or roughened surfaces, sheets, ribbons, strings, or the like.

These definitions are not intended to be limiting, and these terms may be defined with additional language in the remaining portion of the specification.

Figure 1:
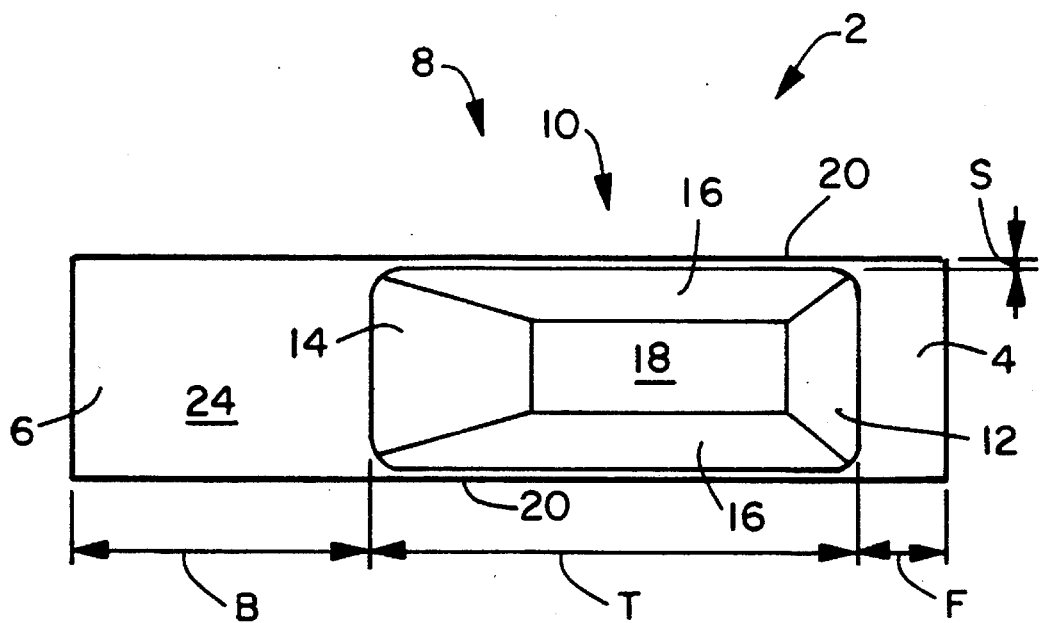
FIG. 1 is a bottom plan view of a preferred embodiment of the present invention.
Figure 2:
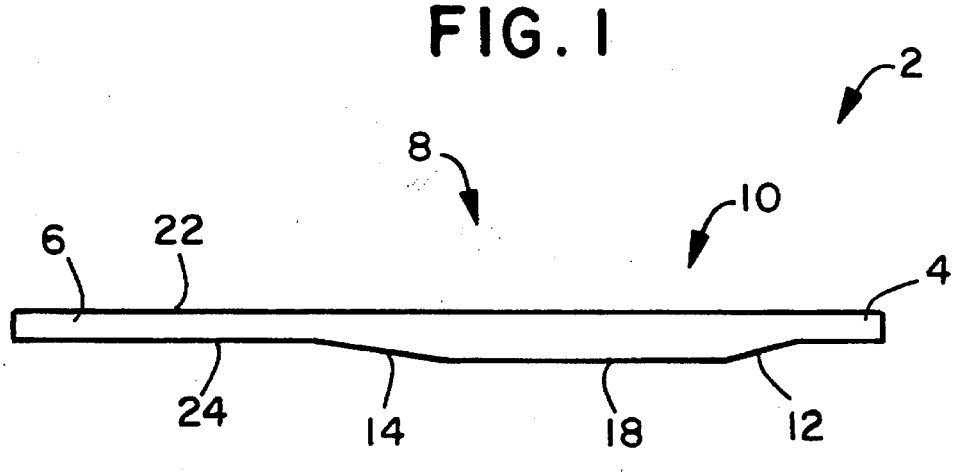
FIG. 2 is a side elevational view of the embodiment in FIG. 1.
Figure 3:
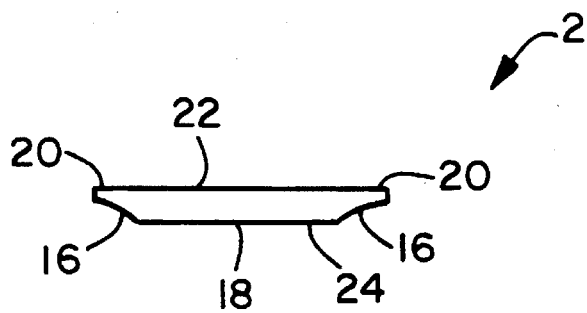
FIG. 3 is an end elevational view of the embodiment in FIG. 1.

Referring to FIGS. 1–3, there is illustrated absorbent article 2 of the present invention having any desired shaped, such as rectangular, square, racetrack, hourglass, circular, oval, or the like. As illustrated in FIG. 1, absorbent article 2 is rectangular in shape and has a length of about 14 inches and a width of about 4 inches. Absorbent article 2 generally comprises front end area 4, back end area 6, crotch area 8, and target area 10. Generally, crotch area 8 is considered the middle one-third, as measured along the longitudinal axis, of absorbent article 2. Target area 10 may or may not be positioned entirely within crotch area 8. For boys, target area 10 generally, will overlap crotch area 8 and front end area 4 as illustrated in FIG. 1. For girls, it may be desired to center target area 10 within crotch area 8. Front end area 4 is also illustrated in length by the letter "F", back end area 6 is illustrated in length by the letter "B", and target area 10 is illustrated in length by letter "T". Target area 10 comprises central zone 18, front transition area 12, back transition area 14, and a pair of side transition areas 16. Absorbent article 2 further comprises side areas 20, which are illustrated in their width dimension by the letter "S". Absorbent article 2 further includes top surface 22 and bottom surface 24.

In this particular embodiment, absorbent article 2 is a mixture of cellulosic fibers and particles of superabsorbent material. Absorbent article 2 can also comprise other fibrous materials, such as synthetic fibers, and mixtures of synthetic and cellulosic fibers. Suitable superabsorbent materials include inorganic materials such as silica gels or organic compounds such as cross-linked polymers. Examples include polyacrylamides, polyvinyl alcohol, polyacrylates, various grafted starches, and the like. If desired, absorbent article 2 can be wrapped in a thin tissue wrap (not shown) to maintain its integrity.

A unique feature of the present invention is the inverse relation between basis weights and densities between central zone 18 and end areas 4, 6. In producing article 2, cellulosic fibers and particles of superabsorbent material are delivered to a forming chamber at a constant ratio to each other. In other words, the fluff to SAM ratio remains constant even though the flow rate of cellulose and SAM to the forming chamber may vary. By selectively varying the flow rate of fluff and SAM to the forming chamber, different amounts of fluff and SAM are distributed within absorbent article 2.

In a preferred embodiment, target area 10 has a higher average basis weight of absorbent material than end areas 4, 6 and side areas 20. Within target area 10, central zone 18 has a higher average basis weight than transition areas 12, 14, 16. Within these transition areas 12, 14, 16, the basis weight decreases to relatively constant basis weights in end areas 4, 6, and side areas 20. The degree of change in basis weight, and densities as hereafter described, can vary as necessary to suit the particular absorbent article size, shape, and absorbent material of which it is made. The present invention also contemplates that the basis weights of front end area 4, back end area 6, and side areas 20 may differ. For example, front end area 4 may have an average basis weight higher than back end area 6, while back end area 6 may have a higher average basis weight than side areas 20; all of these basis weights being less than the basis weight of target area 10. After absorbent article 2 has been formed as described above, it is selectively compressed to its final shape.

In this embodiment, target area 10 has a lower average density than end areas 4, 6, and a higher average density than side areas 20. If desired, front end area 4 and back end area 6 can have different densities, each of which will be higher than the density of target area 10. As viewed in FIG. 2, it is seen that central zone 18 has a relatively constant thickness, basis weight, and density; and end areas 4, 6 have relatively constant thicknesses, basis weights, and densities. From central zone 18 to either end area 4, 6, the thickness and basis weight decreases, but density increases. From central zone 18 to either side area 20, thickness, basis weight, and density will decrease.

Since target zone 10 has a high basis weight and low density, it can rapidly absorb fluids therein. Because of an increasing capillary force resulting from increasing densities between central zone 18 and end areas 4, 6, the absorbed liquid will tend to transfer or wick from the lower density area to the higher density areas. Because of this wicking from central zone 18 or, target area 10 towards end areas 4, 6, more efficient use of the absorbent material of article 2 is realized. Since target area 10 has a higher average density than side areas 20, wicking in the lateral or cross direction towards side areas 20 will tend to be reduced. However, overflow conditions may exist that override these capillary forces. Similarly, since end areas 4, 6 have a higher average density than side areas 20, transfer or wicking of liquid from end areas 4, 6 to side areas 20 also is reduced.

Target area 10 preferably has an average basis weight between about 300 to about 1500 grams per square meter (gsm), and more preferably 900 gsm. Target area 10 preferably has an average density between about 0.05 to about 0.20 grams per cubic centimeter (gcc), and more preferably about 0.12 gcc.

End areas 4, 6 preferably have an average basis weight between about 50 to about 900 gsm, and more preferably about 750 gsm. End areas 4, 6 have a preferred average density between about 0.08 to about 0.30 gcc, and more preferably about 0.17 gcc.

Side areas 20 preferably have a basis weight between about 40 to about 800 gsm, and more preferably about 750 gsm. Side areas 20 preferably have an average density between about 0.03 to about 0.14 gcc, and more preferably about 0.08 gcc.

Figure 4:
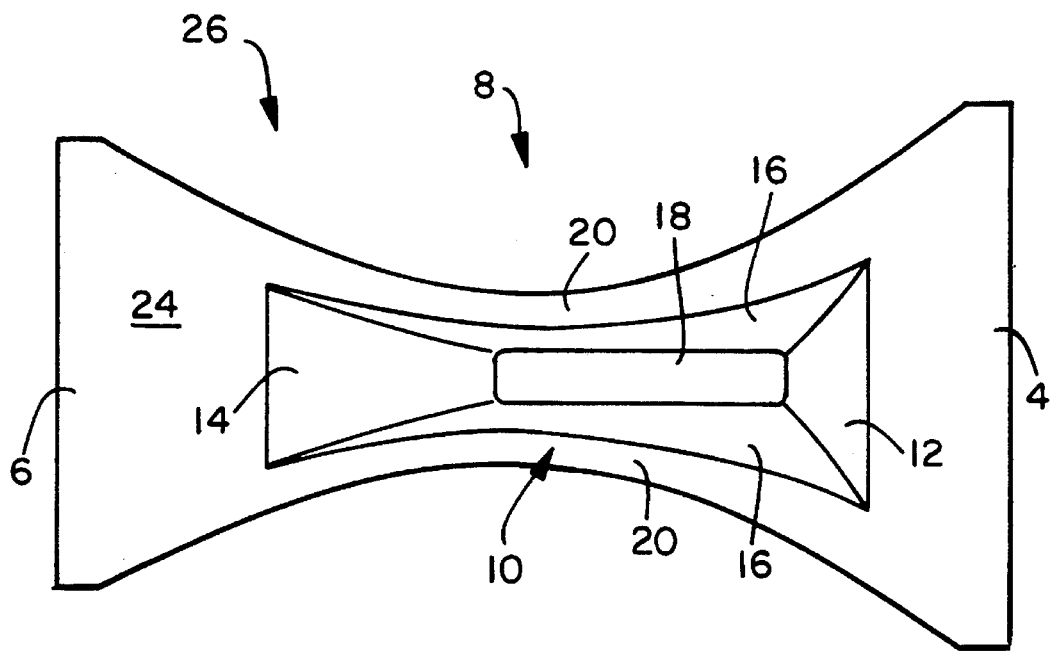
FIG. 4 is a bottom plan view of a modification of the embodiment in FIG. 1.

Turning now to FIG. 4, there is illustrated absorbent article 26, which is a modification of article 2, in which crotch area 8 is narrower than end areas 4, 6. In this particular embodiment, crotch area 8 has a minimum crotch width equal to or less than about 3 inches. Absorbent article 26 permits the absorbent structure to fit closely and conformably to the perineum area.

Figure 5:
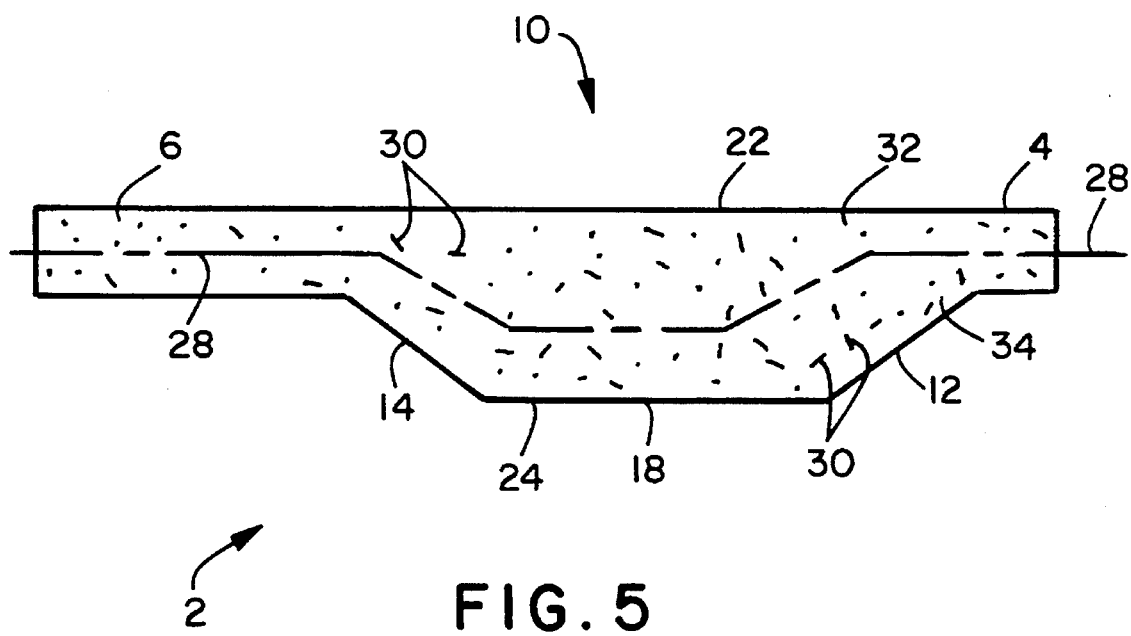
FIG. 5 is a side elevational view similar to FIG. 2 illustrating the presence of superabsorbent material.

Referring now to FIG. 5, absorbent article 2 is a uniform mixture of fibrous materials and particles 30 of superabsorbent material. Although the fibrous material is not illustrated, it is present in the areas surrounding particles 30. Longitudinal center plane 28 equally divides absorbent article 2 into a top half 32 and bottom half 34. As illustrated, longitudinal center plane 28 is not flat, but dips downwardly to accommodate target area 10. As earlier described, the process of making absorbent article 2 maintains a constant ratio between fluff fibers and particles, and varies the amount of the fluff and SAM particle mixture along both the longitudinal and transverses axes so as to vary the basis weight of absorbent material within absorbent article 2.

Figure 6:
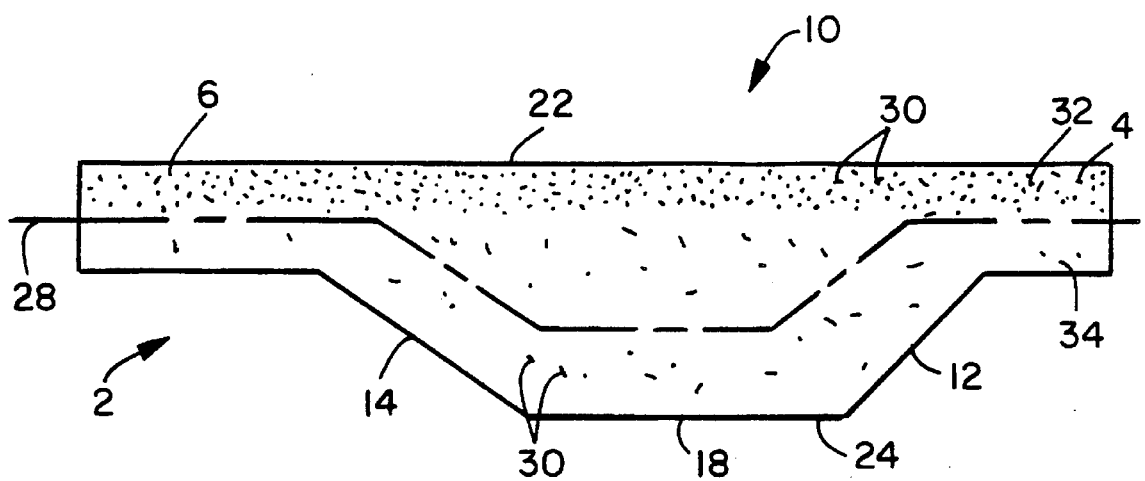
FIG. 6 is similar to FIG. 5 illustrating the superabsorbent material concentrated near the top surface.

FIG. 6 is similar to FIG. 5 except that particles 30 are more highly concentrated in top half 32. Preferably, more than 60 percent of the SAM particles 30 are in top half 32.

Figure 7:
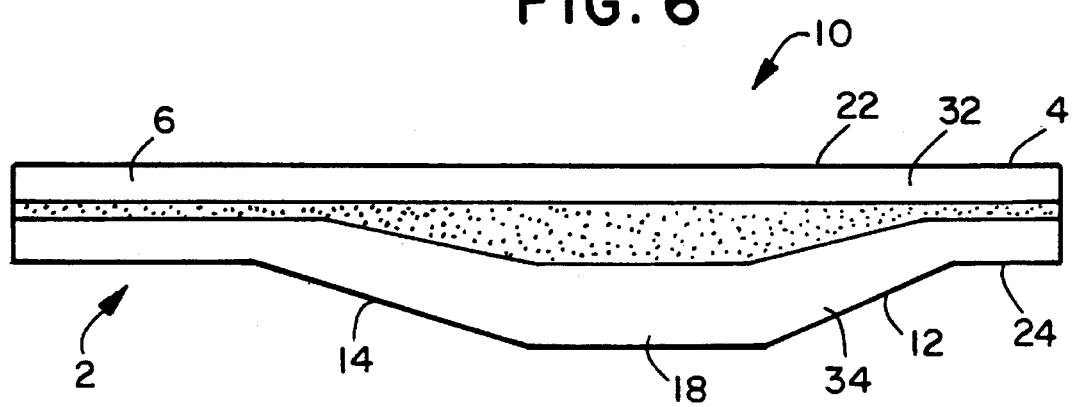
FIG. 7 illustrates the superabsorbent material in a discrete lamina.

FIG. 7 illustrates SAM particles 30 isolated within a generally discrete lamina in the cellulosic fluff. It may be necessary to use a tissue wrap material at the boundaries of particles 30 and fluff to maintain the discreteness of the SAM lamina.

Figure 8:
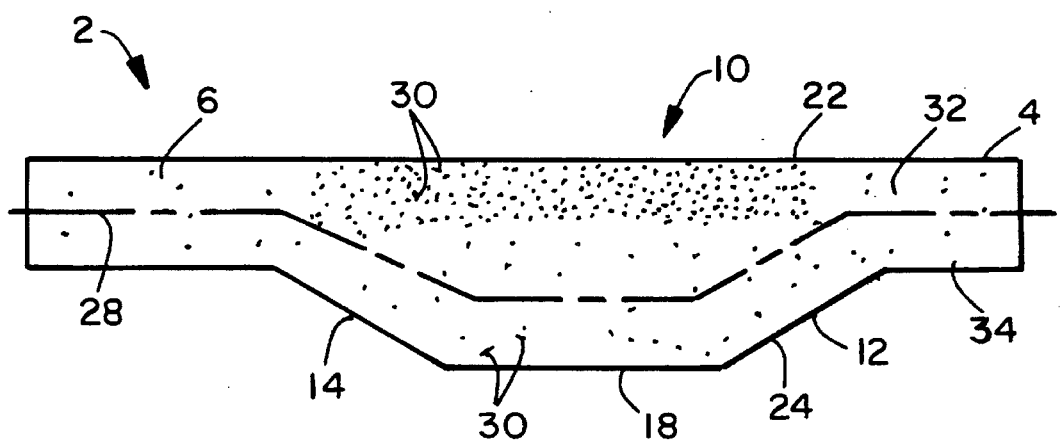
FIG. 8 is similar to FIG. 6 illustrating the superabsorbent material in an intermediate area.

FIG. 8 is similar to FIG. 6 except that end areas 4, 6 have substantially fewer or no particles 30 therein. It is preferred that more than 60 percent of particles 30 be in top half 32.

Figure 9:
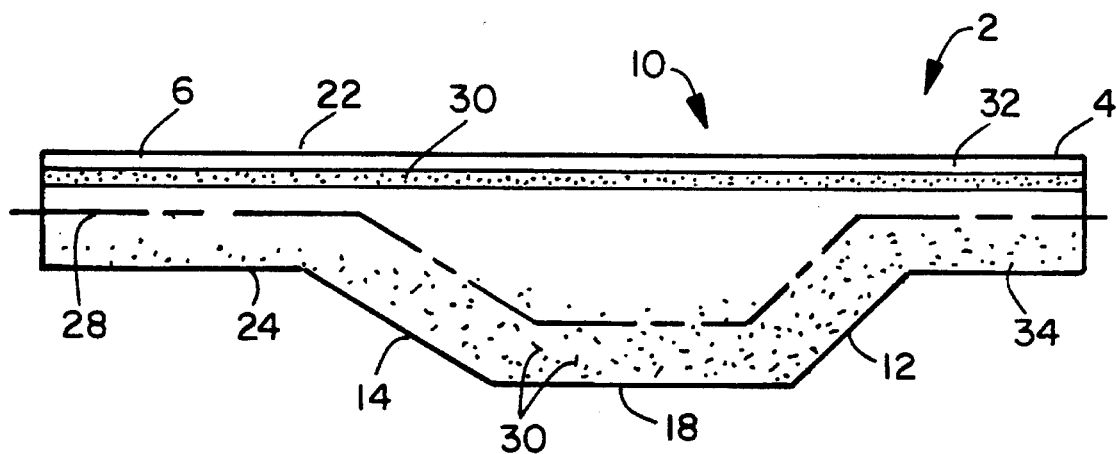
FIG. 9 illustrates a discrete lamina of superabsorbent material in the top half and non-layered superabsorbent material in the bottom half.

FIG. 9 illustrates particles 30 in top half 32 in a generally discrete lamina, while particles 30 in bottom half 34 are mixed with other fibrous material.

Figure 10:
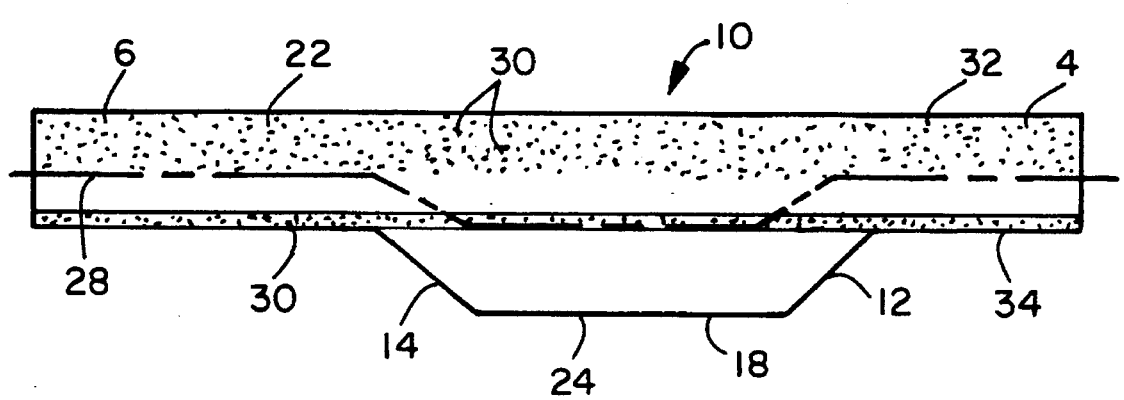
FIG. 10 illustrates a discrete lamina of superabsorbent material in the bottom half and non-layered superabsorbent material in the top half.

FIG. 10 is the reverse of FIG. 9, in that particles 30 in top half 32 are mixed with fibrous material, while SAM particles 30 in bottom half 34 are in a generally discrete lamina.

Figure 11:
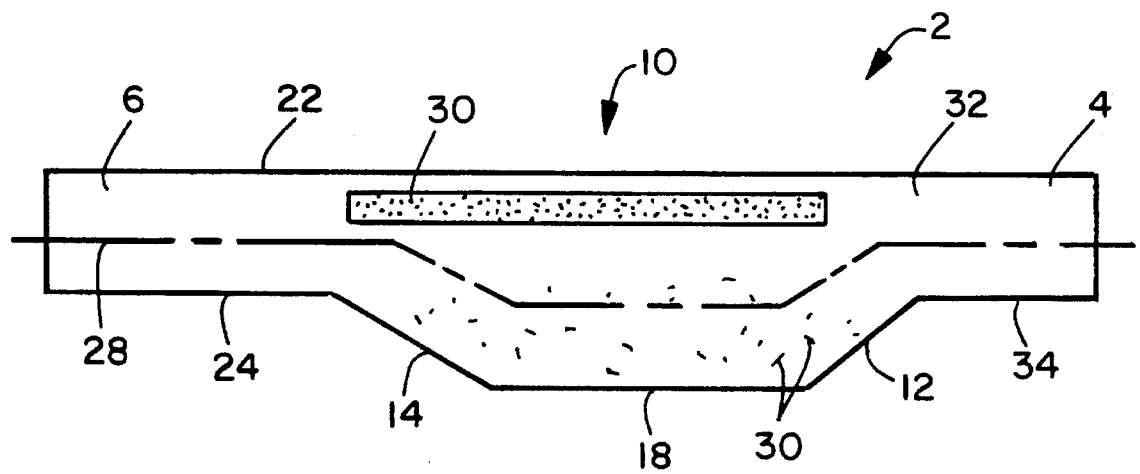
FIG. 11 is similar to FIG. 9 with the superabsorbent material in an intermediate area.

FIG. 11 is similar to FIG. 9 except that end areas 4, 6 have substantially fewer or no particles 30.

Although a preferred embodiment of article 2 has varying basis weights and densities as described above, the present invention also includes a modification in which article 2 has a constant or uniform basis weight throughout with the densities varying as described above.

Figure 12:
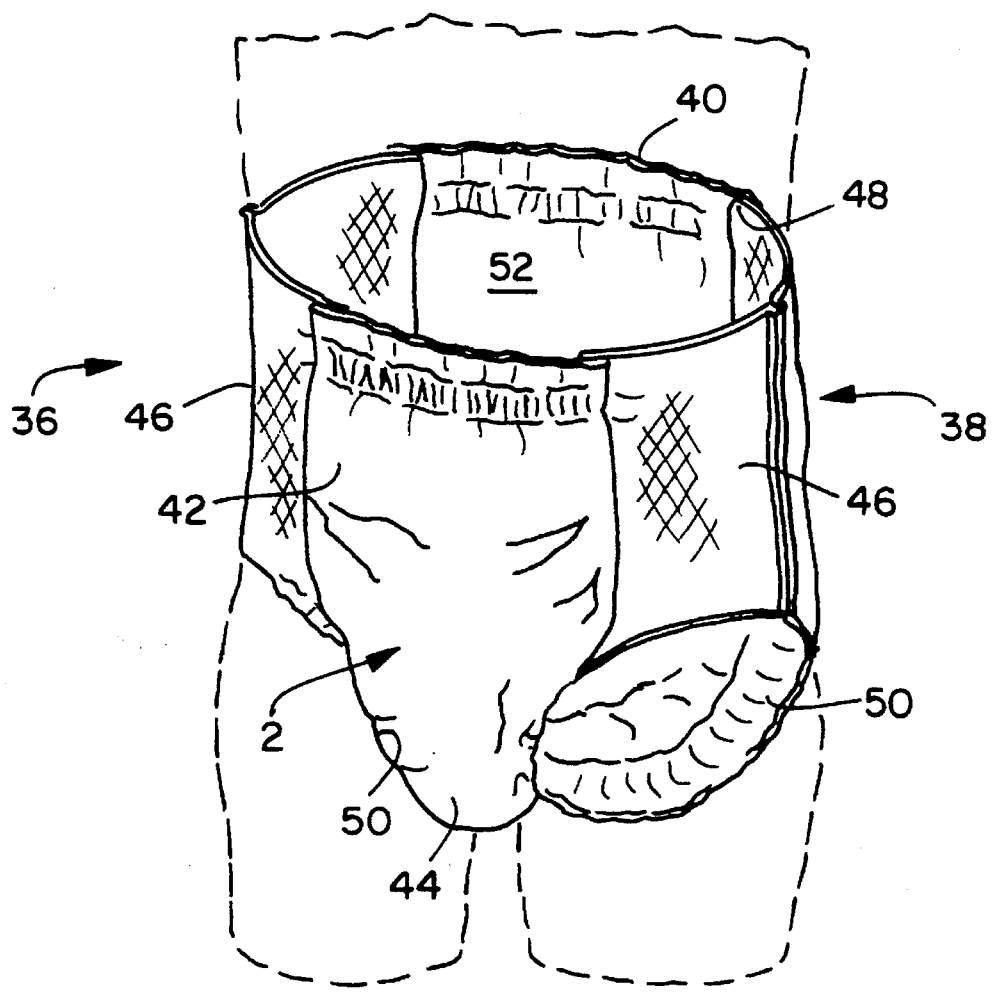
FIG. 12 is a perspective view of a child's training pant incorporating a preferred embodiment of the present invention.
Figure 13:
FIG. 13 is a top plan view of the training pant in FIG. 12 with the seams torn away and the training pant laid flat.
Figure 13:
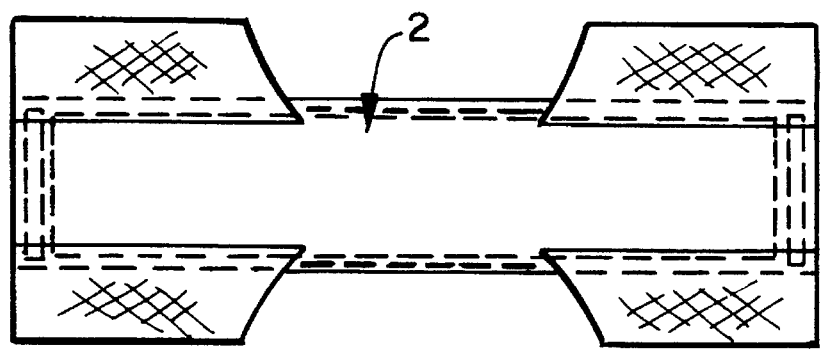

Referring now to FIGS. 12 and 13, absorbent article 2 can be used in various disposable garments, such as a child's training pant 36 comprising main body 38 that includes back portion 40, front portion 42, crotch portion 44, and sides 46 forming waist opening 48, leg openings 50, and interior space 52. A more detailed description of one type of child's training pant and the incorporation of an absorbent structure therein is described in U.S. Pat. No. 4,940,464 to Van Gompel, the contents of which are incorporated by reference herein.

Determination of the concentrations of superabsorbent particles 30 within absorbent article 2 are known within the art. One such means is described in U.S. Pat. No. 4,699,823 to Kellenberger, the contents of which are incorporated by reference herein.

While this invention has been described as having preferred embodiments, it will be understood that it is capable of further modifications. This application is therefore intended to cover any variations, equivalents, uses, or adaptations of the invention following the general principles thereof, and including such departures from the present disclosure as come within known or customary practice in the art to which this invention pertains and falls within the limits of the appended claims.

What is claimed is:

1. An absorbent article, comprising:

a layer comprising generally oppositely disposed end areas, a target area between said end areas, and a top surface and a bottom surface defining therebetween a layer thickness, said target area having a higher average basis weight and a lower average density than one of said end areas, said layer further comprising an absorbent fibrous material and superabsorbent particles, all of said superabsorbent particles being in a discrete lamina.

2. An absorbent article, comprising:

a layer comprising generally oppositely disposed end areas and generally oppositely disposed side areas, a target area between said end areas, and a top surface and a bottom surface defining therebetween a layer thickness, said target area having a higher average basis weight and a lower average density than one of said end areas, said target area having a higher average basis weight and a higher average density than said side areas, said one end area having a higher average density than said side areas, said layer further comprising an absorbent fibrous material and superabsorbent particles, at least a portion of said superabsorbent particles being in a discrete lamina.

3. An absorbent article, comprising:

a layer comprising generally oppositely disposed end areas and generally oppositely disposed side areas, a target area between said end areas, and a top surface and a bottom surface defining therebetween a layer thickness, said target area having a higher average basis weight and a lower average density than said end areas, one of said end areas having a higher average density than said side areas, said layer further comprising an absorbent fibrous material and superabsorbent particles, at least a portion of said superabsorbent particles being in a discrete lamina.

* * * * *